United States Patent [19]

Newman

[11] 4,006,159
[45] Feb. 1, 1977

[54] SUBSTITUTED 1,2,4-TRIAZOLE CARBOXAMIDES

[75] Inventor: Howard Newman, Monsey, N.Y.

[73] Assignee: American Cyanamid Company, Stamford, Conn.

[22] Filed: Mar. 14, 1975

[21] Appl. No.: 558,611

[52] U.S. Cl. .......................... 260/308 R; 424/232; 424/269
[51] Int. Cl.² .............. A61K 31/41; A61K 31/625; C07D 249/10
[58] Field of Search ................ 260/308 R; 424/269

[56] References Cited

UNITED STATES PATENTS

| 3,308,131 | 3/1967 | McKusick | 260/308 R |
| 3,927,216 | 12/1975 | Witkowski et al. | 424/269 |

OTHER PUBLICATIONS

Elderfield, Heterocyclic Compounds, vol. 7, (New York, 1961), pp. 446–450.

Primary Examiner—Alton D. Rollins
Attorney, Agent, or Firm—Neal O. Willmann

[57] ABSTRACT

This disclosure describes mixtures of novel acyl-substituted 1,2,4-triazole-3-carboxamides which possess antiviral activity.

6 Claims, No Drawings

SUBSTITUTED 1,2,4-TRIAZOLE CARBOXAMIDES

BRIEF SUMMARY OF THE INVENTION

This invention relates to new organic compounds and, more particularly, is concerned with mixtures of novel acyl-substituted 1,2,4-triazole-3-carboxamides which may be represented by the following structural formulae:

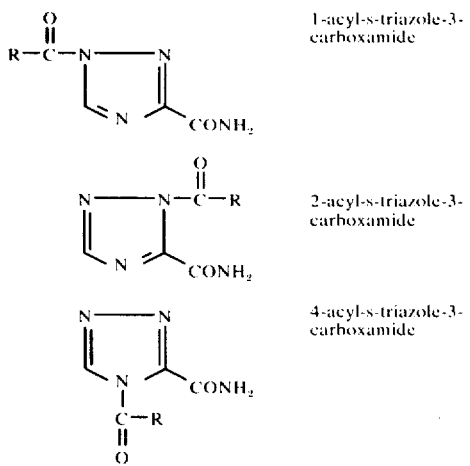

wherein each mixture consists of all three forms wherein R is the same in each form and wherein R is hydrogen; alkyl having up to 15 carbon atoms; cycloalkyl having from 3 to 8 carbon atoms; phenyl; ortho-, meta-, or para-hydroxyphenyl; ortho-, meta-, or para-methoxyphenyl; or adamantyl. A preferred embodiment of the present invention consists of those mixtures of all three forms wherein R is the same in each form and wherein R is alkyl having up to 8 carbon atoms, cycloalkyl having from 5 to 7 carbon atoms, or phenyl.

DETAILED DESCRIPTION OF THE INVENTION

The novel mixtures of the present invention may be readily prepared by treating 1,2,4-triazole-3-caboxamide with an acid anhydride of the formulae:

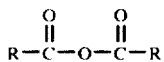

wherein R is as hereinabove defined. This reaction is preferably carried out in an excess of the acid anhydride as solvent at a temperature of from about 150° C to about 160° C. for a period of time of from about 15 minutes to a few hours. The novel mixtures of the present invention may also be prepared by treating 1,2,4-triazole-3-carboxamide with and acid halide of the formulae:

wherein X is chloro or bromo and R is as hereinabove defined. This reaction is preferably carried out in an inert solvent such as diethyl ether, tetrahydrofuran, acetonitrile, or dimethylformamide in the presence of an acid acceptor such as triethylamine at room temperature for a period of time of from about 12 hours to about 24 hours. This reaction may also be carried out by treating 1,2,4-triazole-3-carboxamide sodium salt with the acid halide in the presence of pellets of 4A molecular sieves. The novel mixtures of the present invention are readily isolated from the above reaction mixtures and purified by the usual techniques which are commonplace in the art.

The novel mixtures of the present invention have been found to be highly useful as antiviral agents in mammals when administered orally in amounts ranging from about 0.2 mg. to about 25 mg. per kg. of body weight per day. A preferred dosage regimen for optimum results would be from about 0.5 mg. to about 6 mg. per kg. of body weight per day, and such dosage units are employed that a total of from about 35 mg. to about 420 mg. of the mixture for a subject of about 70 kg. body weight are administered in a 24 hour period.

The antiviral mixtures of the present invention may be orally administered, for example, with an inert diluent or with an assimilable edible carrier, or they may be enclosed in hard or soft shell gelatin capsules, or they may be compressed into tablets, or they may be incorporated directly with the food of the diet. For oral therapeutic administration, the mixtures may be incorporated with excipients and used in the form of tablets, troches, capsules, elixirs, suspensions, syrups, wafers, and the like. Such compositions and preparations should contain at least 0.1% of antiviral mixture. The percentage of active ingredient in the compositions and preparations may, of course, be varied and may conveniently be between about 5% to about 25% of the weight of the unit. The amount of mixture in such therapeutically useful compositions is such that a suitable dosage will be obtained. Preferred compositions or preparations according to the present invention are prepared so that an oral dosage unit form contains between about 1 and 200 milligrams of antiviral mixtures.

The tablets, troches, pills, capsules and the like may also contain the following: a binder such as gum tragacanth, acacia, corn starch or gelatin; an excipient such as dicalcium phosphate; a disintegrating agent such as corn starch, potato starch, alginic acid and the like; a lubricant such as magnesium stearate; and a sweetening agent such as sucrose, lactose or saccharin may be added or a flavoring agent such as peppermint, oil of wintergreen, or cherry flavoring. When the dosage unit form is a capsule, it may contain, in addition to materials of the above type, a liquid carrier such as a fatty oil. Various other materials may be present as coatings or to otherwise modify the physical form of the dosage unit. For instance, tablets, pills or capsules may be coated with shellac, sugar or both. A syrup or elixir may contain the active mixtures, sucrose as a sweetening agent, methyl and propylparabens as preservatives, a dye and flavoring such as cherry or orange flavor. Of course, any material used in preparing any dosage unit form should be pharmaceutically pure and substantially non-toxic in the amounts employed.

Inhalation therapy of the antiviral mixtures of the present invention is also contemplated. Medicaments for inhalation therapy are usually dispensed as sprays from solutions either using a pressurized gas source for a separate solution in a spray device or as a self-contained gas source mixed with the medicament in a pressure dispensing container. Most commonly, the antiviral mixtures may be dissolved in a volatile solvent such as a chlorofluoroalkane propellant and upon administration the solvent evaporates to give an inhalable powder. Less commonly, the antiviral mixtures may be suspended as a powder in a propellant and dispersed as a dry aerosol directly. For effective inhalation therapy where the drug is to be deposited in the oral passage or upper respiratory tract, it has been recognized that a particle size greater than 10 microns is desired.

The antiviral mixtures of the present invention are preferably administered to a warm-blooded mammal prior to viral infection in order to prevent or ameliorate the infection, soon after known exposure to infection, or upon recognition of symptoms in order to treat the infection and minimize its systemic effects.

The novel mixtures of the present invention possess antiviral activity as demonstrated by typical mixtures of the present invention in the following test procedure.

Taconic Farms female white mice, weighing 20–24 g. were placed in groups of 5 mice. Each mouse was infected intranasally with 0.5 ml. of a $10^{-1.6}$ dilution of influenza $A_2$ (England strain) in brain-heart infusion broth. In this test the mice were treated orally, immediately after infection and again 4 hours later with the indicated dose of a test compound in 1 ml. of 0.2% agar. In each test one group of 15 infected mice was left untreated as a control. The criterion for a compound to be accepted as having antiviral activity is as follows: In the first test if 2 or more of 5 mice survive a 14 day test period the compound is retested in two groups of 5 mice. The compound is considered active if 5 or more of the total of 15 mice survive for 14 days. In this test the compound 1-$\beta$-D-ribofuranosyl-1H-1,2,4-triazole-3-carboxamide, a known antiviral agent as reported in Science 77, 705 (1972) and J. Med. Chem. 15, 1150 (1972), was also tested as a drug control, with a single oral dose immediately after infection. The results of this test appear in the following table, wherein the mixtures have been designated as follows:

Mixture I 1-acetyl-s-triazole-3-carboxamide + 2-acetyl-s-triazole-3-carboxamide + 4-acetyl-s-triazole-3-carboxamide Mixture II 1-butyryl-s-triazole-3-carboxamide + 2-butyryl-s-triazole-3-carboxamide + 4-butyryl-s-triazole-3-carboxamide Mixture III 1-heptanoyl-s-triazole-3-carboxamide + 2-heptanoyl-s-triazole-3-carboxamide + 4-heptanoyl-s-triazole-3-carboxamide Mixture IV 1-benzoyl-s-triazole-3-carboxamide + 2-benzoyl-s-triazole-3-carboxamide + 4-benzoyl-s-triazole-3-carboxamide Mixture V 1-cyclohexylcarbonyl-s-triazole-3-carboxamide + 2-cyclohexylcarbonyl-s-triazole-3-carboxamide + 4-cyclohexylcarbonyl-s-triazole-3-carboxamide Mixture VI 1-salicyloyl-s-triazole-3-carboxamide + 2-salicyloyl-s-triazole-3-carboxamide + 4-salicyloyl-s-triazole-3-carboxamide

TABLE I

| Mixture | Dose mg./kg. of body weight | Alive/Total (14 days post infection) |
|---|---|---|
| I | 200 | 8/15 |
| II | 200 | 9/15 |
| III | 200 | 6/15 |
| IV | 200 | 8/15 |
| V | 200 | 6/15 |
| VI | 200 | 5/15 |
| treated controls | 200 | 5/15 |

TABLE I-continued

| Mixture | Dose mg./kg. of body weight | Alive/Total (14 days post infection) |
|---|---|---|
| untreated controls | 0 | 0/15 |

The invention will be described in greater detail in conjunction with the following specific examples.

EXAMPLE 1

Preparation of 1(and 2 and 4)-Acetyl-s-triazole-3-carboxamide

A mixture of 0.2 g. of 1,2,4-triazole-3-carboxamide and 0.5 ml. of acetic anhydride is heated on an oil bath at a temperature of 150° C. for 20 minutes. The wet solid mass is triturated with diethyl ether and collected and washed with diethyl ether yielding 0.2 g. of colorless solid. This solid is recrystallized from acetonitrile giving a colorless solid, m.p. 212°–215° C. (dec).

EXAMPLE 2

Preparation of 1(and 2 and 4)-Butyryl-s-triazole-3-carboxamide

A suspension of 2 g. of 1,2,4-triazole-3-carboxamide and 7.5 g. of butyric anhydride is placed in an oil bath preheated to 155°–160° C. and heated at this temperature for 30 minutes. The residue is triturated with diethyl ether and returned to the oil bath with an additional 7.5 g. of butyric anhydride and heated for 30 minutes. The reaction mixture is allowed to cool. The solid which forms is triturated with diethyl ether and collected yielding 2.6 g. of colorless solid. The product is recrystallized from dry acetonitrile yielding 0.6 g. of colorless solid, m.p. 186°–188° C. (dec.).

EXAMPLE 3

Preparation of 1(and 2 and 4)-Heptanoyl-s-triazole-3-carboxamide

To a cooled, stirred mixture of 3 g. of 1,2,4-triazole-3-carboxamide and 4 g. of heptanoic anhydride in 125 ml. of anhydrous diethyl ether is added rapidly 2.75 g. of triethylamine. The cooling bath is removed and the mixture is stirred at room temperature for 17.5 hours. The heterogeneous mixture is filtered, washed with diethyl ether, cold water and then diethyl ether, dried for about 15 minutes and then dried in vacuo yielding 4 g. of colorless solid. The solid is extracted in hot dry acetonitrile and on cooling to room temperature the product is collected, washed with acetonitrile and dried in vacuo, yielding 0.4 g. of colorless crystals, m.p. 184°–187° C. (dec.).

EXAMPLE 4

Preparation of 1(and 2 and 4)-Benzoyl-s-triazole-3-carboxamide

To a cooled, stirred mixture of 3 g. of 1,2,4-triazole-3-carboxamide and 4 g. of benzoyl chloride in 125 ml. of anhydrous diethyl ether is added rapidly 2.75 g. of triethylamine. The cooling bath is removed and the mixture is stirred at room temperature for 18 hours. The heterogeneous mixture is filtered and washed successively with diethyl ether, cold water and then diethyl ether and dried in vacuo for 4 hours yielding 4 g. of colorless solid. This solid is extracted with hot, dry acetonitrile and cooled yielding a solid product which is collected, washed with acetonitrile and dried in vacuo, yielding 1 g. of product, m.p. 174°–178° C. (dec.).

EXAMPLE 5

Preparation of 1(and 2 and 4)-cyclohexylcarbonyl-2-triazole-3-carboxamide

To a cooled, stirred mixture of 3 g. of 1,2,4-triazole-3-carboxamide and 4 g. of cyclohexylcarbonyl chloride in 125 ml. of anhydrous diethyl ether is added rapidly 2.75 g. of triethylamine. The cooling bath is removed and the mixture is stirred at room temperature for 17.5 hours. The mixture is then filtered, washed successively with diethyl ether, cold water and then diethyl ether and dried in vacuo for 4 hours, yielding 4 g. of colorless solid. This solid is extracted with hot dry acetonitrile. The product is collected, washed with acetonitrile and dried in vacuo, yielding 1 g. of colorless crystals, m.p. 184°–187° C. (dec.).

EXAMPLE 6

Preparation of 1(and 2 and 4)-Adamantylcarbonyl-s-triazole-3-carboxamide

To a cooled, stirred mixture of 2 g. of 1,2,4-triazole-3-carboxamide and 5.4 g. of adamantylcarbonyl chloride in 125 ml. of anhydrous diethyl ether is added rapidly 2.75 g. of triethylamine. The cooling bath is removed and the mixture is stirred at room temperature for 23.5 hours. The mixture is filtered and the solid is washed successively with diethyl ether, cold water, diethyl ether and dried in vacuo for 3 hours yielding 4.5 g. of colorless solid. This solid is extracted with hot dry acetonitrile, cooled and washed with acetonitrile yielding 0.4 g. of colorless crystals. The remaining 3.5 g. of acetonitrile insoluble solid is further extracted with acetonitrile, yielding an additional 0.6 g. of product, m.p. 213°–216° C. (dec.).

EXAMPLE 7

Preparation of 1(and 2 and 4)-Salicyloyl-s-triazole-3-carboxamide

To a cooled, stirred mixture of 2 g. of 1,2,4-triazole-3-carboxamide and 5.4 g. salicyloyl chloride in 125 ml. of anhydrous diethyl ether is added rapidly 2.75 g. of triethylamine. The cooling bath is removed and the mixture is stirred at room temperature for 22 hours. The mixture is filtered and the solid is collected and washed successively with diethyl ether, cold water, diethyl ether and dried in vacuo for 4 hours. The solid is extracted with hot, dry acetonitrile. The filtrate is reduced to about half volume by evaporation in vacuo over a warm water bath and filtered to separate a small amount of solid which separates for 2 hours. Further evaporation of the resulting filtrate to a very small volume results in the separation of a solid which is collected, washed with acetonitrile and dried yielding 210 m.p. 125°–135° C. (dec.).

EXAMPLE 8

Alternative preparation of 1(and 2 and 4)-Salicyloyl-s-triazole-3-carboxamide

A 25 ml. portion of dry acetonitrile is added to a mixture of 1.3 g. of the s-triazole carboxamide sodium salt and 2 g. of salicyloyl chloride followed by a few pellets of 4A molecular sieves. The mixture is stirred at room temperature for 16 hours and then filtered through Celite. The colorless solid is obtained on evaporating the filtrate is washed with diethyl ether; yield, 1 g., m.p. 147°–150° C. (dec.). Its infrared spectrum is essentially the same as that obtained from the product in Example 7.

EXAMPLE 9

Preparation of 1(and 2 and 4)-Palmitoyl-s-triazole-3-carboxamide

To a cooled, stirred mixture of 3 g. of 1,2,4-triazole-3-carboxamide and 7.4 g. of palmitoyl chloride in 125 ml. of anhydrous diethyl ether is added rapidly 2.75 g. of triethylamine. The cooling bath is removed and the mixture is stirred. at room temperature for 24 hours. The mixture is filtered and the solid is washed successively with diethyl ether, cold water, diethyl ether and then dried in vacuo for 4 hours. The solid is extracted with hot dry acetonitrile and cooled yielding a colorless solid. The solid is redissolved by heating the mixture and allowed to recrystallize from the clear, colorless solution. The product is collected, washed with acetonitrile and dried in vacuo for 3 hours, yielding 0.75 g., m.p. 145°–160° C. (dec.).

EXAMPLE 10

Preparation of 1(and 2 and 4)-Pivaloyl-s-triazole-3-carboxamide

To a cooled, stirred mixture of 3 g. of 1,2,4-triazole-3-carboxamide and 3.4 g. of pivaloyl chloride in 125 ml. of anhydrous diethyl ether is added rapidly 2.75 g. of triethylamine. The cooling bath is removed and the mixture is stirred at room temperature for 24 hours. The off-white solid is collected by filtration and washed thoroughly with diethyl ether and then cold water. The ether-cold water filtrate deposits another solid almost immediately. This solid is collected by filtration and dried in vacuo for 3.5 hours, yielding 0.22 g. This 0.22 g. is extracted with hot, dry acetonitrile. Concentration of the acetonitrile filtrate to a very small volume gives a colorless, crystalline solid which is collected, washed with a small amount of acetonitrile and dried in vacuo for 2 hours, yielding 50 mg., m.p. 132°–140° C. (dec.).

EXAMPLE 11

Preparation of 1,2,4-triazole-3-carboxamide sodium salt

A 0.6 g. portion of 1,2,4-triazole-3-carboxamide is added to 5.4 ml. of a solution of 1N sodium methoxide in methanol contained in a test tube at room temperature. The mixture is shaken vigorously. Within about ½ to one minute most of the solid dissolves. The mixture is quickly filtered through a sintered glass funnel with vacuum. The light yellow filtrate is allowed to stand and deposits a colorless solid. A portion of methanol is added and the solid is collected, washed with methanol and air dried for one hour yielding 0.3 g. of product.

EXAMPLE 12

| Preparation of Capsule Formulation | |
|---|---|
| Ingredient | Mg. per capsule |
| Mixture of 1(and 2 and 4)-formyl-s-triazole-3-carboxamide | 150 |
| Lactose | 150 |

EXAMPLE 12-continued

| Preparation of Capsule Formulation | |
|---|---|
| Ingredient | Mg. per capsule |
| Magnesium stearate | 5 |

The active ingredients, lactose and magnesium stearate are blended together. The mixture is used to fill hard shell capsules of a suitable size at a fill weight of 305 milligrams per capsule.

EXAMPLE 13

| Preparation of Tablet Formulation | |
|---|---|
| Ingredient | Mg. per tablet |
| Mixture of 1(and 2 and 4)-isovaleryl-s-triazole-3-carboxamide | 150 |
| Sucrose | 100 |
| Corn Starch (for mix) | 50 |
| Corn Starch (for paste) | 50 |
| Magnesium stearate | 5 |

The active ingredients, sucrose, and corn starch (for mix) are blended together. The corn starch (for paste) is suspended in water at a ratio of 10 grams of corn starch per 80 milliliters of water and heated with stirring to form a paste. This paste is then used to granulate the mixed powders. The wet granules are passed through a No. 8 screen and dried at 120° F. The dry granules are passed through a No. 16 screen. The mixture is lubricated with the magnesium stearate and compressed into scored tablets in a suitable tableting machine. Each tablet contains 150 milligrams of active ingredients.

EXAMPLE 14

| Preparation of Oral Syrup Formulation | |
|---|---|
| Ingredient | Amount |
| Mixture of 1(and 2 and 4)-cyclopentylcarbonyl-s-triazole-carboxamide | 450 mg. |
| Sorbitol solution (70% N.F.) | 40 ml. |
| Sodium benzoate | 150 mg. |
| Sucaryl | 90 mg. |
| Saccharin | 10 mg. |
| Red Dye (F.D. & C. No. 2) | 10 mg. |
| Cherry flavor | 50 mg. |
| Distilled water    qs | 100 ml. |

The sorbitol solution is added to 40 milliliters of distilled water and the active ingredients are suspended therein. The sucaryl, saccharin, sodium benzoate, flavor and dye are added and dissolved in the above solution. The volume is adjusted to 100 milliliters with distilled water.

Other ingredients may replace those listed in the above formulation. For example, a suspending agent such as bentonite magma, tragacanth, carboxymethylcellulose, or methylcellulose may be used. Phosphates, citrates or tartrates may be added as buffers. Preservatives may include the parabens, sorbic acid and the like and other flavors and dyes may be used in place of those listed above.

I claim:
1. 1(and 2 and 4)-Octanoyl-s-triazole-3-carboxamide.
2. 1(and 2 and 4)-Acetyl-s-triazole-3-carboxamide.
3. 1(and 2 and 4)-Butyryl-s-triazole-3-carboxamide.
4. 1(and 2 and 4)-Benzoyl-s-triazole-3-carboxamide.
5. 1(and 2 and 4)-Cyclohexylcarbonyl-s-triazole-3-carboxamide.
6. 1-(and 2 and 4)-Salicycloyl-s-triazole-3-carboxamide.

* * * * *